United States Patent [19]

Heckele

[11] 4,271,829
[45] Jun. 9, 1981

[54] ENDOSCOPE WITH DISTANCE MEASURING DEVICE

[75] Inventor: Helmut Heckele, Knittlingen, Fed. Rep. of Germany

[73] Assignee: Richard Wolf GmbH, Knittlengen, Fed. Rep. of Germany

[21] Appl. No.: 30,452

[22] Filed: Apr. 16, 1979

[30] Foreign Application Priority Data

Apr. 28, 1978 [DE] Fed. Rep. of Germany ....... 2818760

[51] Int. Cl.³ .............................................. A61B 1/06
[52] U.S. Cl. ...................................... 128/6; 356/383; 356/1; 33/125 A
[58] Field of Search ........................................ 128/3–8; 350/96.26; 356/241, 383, 1; 33/125 A

[56] References Cited

U.S. PATENT DOCUMENTS

| 3,817,631 | 6/1974 | Kawahara | 128/6 X |
| 3,817,635 | 6/1974 | Kawahara | 128/6 X |
| 3,819,267 | 6/1974 | Kawahara | 128/6 X |
| 3,873,211 | 3/1975 | Watson | 356/241 X |

Primary Examiner—Kyle L. Howell
Assistant Examiner—Arthur S. Rose
Attorney, Agent, or Firm—Kinzer, Plyer, Dorn & McEachran

[57] ABSTRACT

This invention relates to endoscopes of the kind incorporating a device for measuring the distance between the subject and the objective or objective lens of the optical system of the endoscope.

According to the invention the measuring device comprises means for passing two thin and visible light rays along the longitudinal direction of the endoscope, and reflector means for deflecting these light rays at the distal end of the endoscope next to the objective lens of the optical system. The reflector means are spaced apart from each other to form measuring rays the first one of said rays being deflected by deflector means into a fixed and approximately parallel position with respect to the longitudinal axis of the objective lens and the second one of said rays being deflected by a rotatable reflector in a plane of the fixed deflection ray with a variable angle. A rotatable scale is provided at the proximal end of the endoscope to read off the angle from an angular position referred to the longitudinal axis of the objective lens and serving as zero position, until it intersects the fixed measuring ray in the plane of the subject.

1 Claim, 5 Drawing Figures

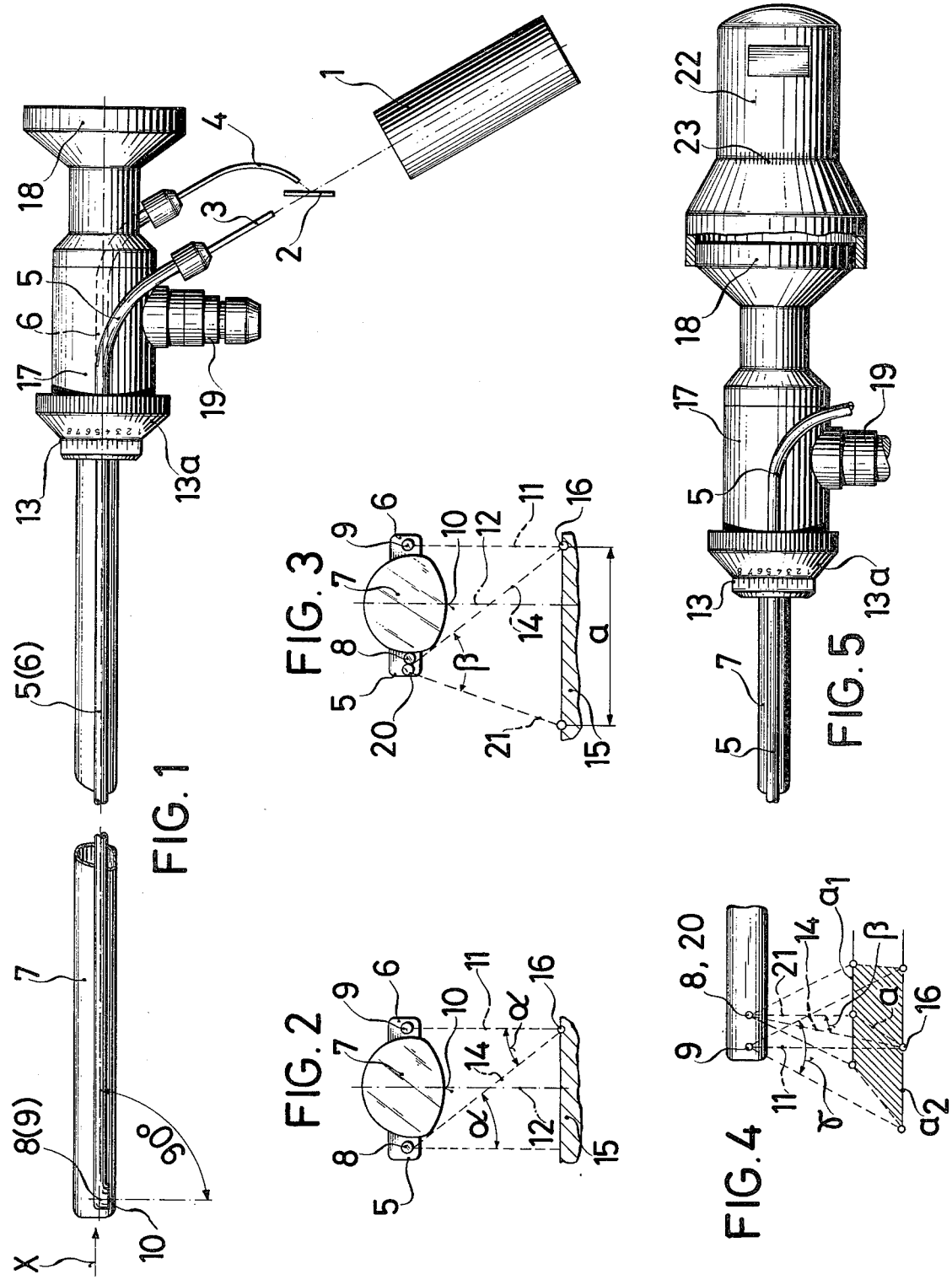

ENDOSCOPE WITH DISTANCE MEASURING DEVICE

BACKGROUND OF THE INVENTION

The present invention relates to endoscopes and particularly to endoscopes fitted with a device for measuring the distance between the subject and the objective or objective lens of the optical system of the endoscope.

In the field of endoscopy the demand is made more and more frequently to determine the distance of human organs or technical parts to be examined from the objective of the endoscope, and the dimensions of a subject. For this purpose use has been made already of measuring rods to be passed through the shaft of the endoscope which are advanced toward the subject during observation, during which process the distance of the subject from the objective can be read off on a proximal graduation on the measuring rods. With this method, however, it is not possible to measure distance accurately, apart from the fact that manipulation of the instrument is made more difficult for the doctor and a burden is placed on the patient.

For this reason it is an object of the invention to dispense with such measuring rods for measuring distances between subject and objective of the optical system of the endoscope, and to enable the doctor to perform the measurement directly during the objservation or examination of the subject without coming into contact with it.

SUMMARY OF THE INVENTION

According to the invention, this object is achieved by passing two, thin, visible, preferably coloured light rays along the longitudinal direction of the endoscope and deflecting them at the distal end by reflectors next to the objective of the optics system of the endoscope, spaced apart from each other, as measuring rays, the first one being deflected into a fixed and parallel or approximately parallel position with respect to the axis of the objective lens and the second one being deflected by a rotatable reflector in a plane of the fixed deflection ray with a variable angle which can be read off as distance at a rotatable scale at the proximal end, from an angular position referred to the axis of the objective lens and serving as zero position, until it intersects the fixed measuring ray in the plane of the subject.

Thus, a construction according to the invention gives the doctor the capability of being able to perform a distance measurement by purely optical means during the observation of the subject by using endoscopes with lateral, straight or prograde objectives, during which he merely has to turn a proximal manipulator with an indicating scale so that in this way the deflection angle of the rotatable reflector with the deflected measuring ray, and thus the distance of the subject from the objective, can be determined via a calibrating table, or the scale itself can be calibrated in units of distance measurement.

By using this optical distance measuring system according to the invention it is also possible to perform length measurements of the subject by proceding in such a way, according to a further development, that in the plane of the first and second measuring ray a third thin measuring ray can be deflected, apart from the deflection of the second measuring ray, by a manipulator provided proximally with an indicating scale at an angle to the intersecting second measuring way, by means of which arrangement the distance of the point of intersection of the third measuring ray with the plane of the subject from the point of intersection of the second measuring ray with the fixed measuring ray is representative of a longitudinal dimension of the subject.

BRIEF DESCRIPTION OF THE DRAWINGS

In order that the invention may be more clearly understood, reference will now be made to the accompanying drawings which show certain embodiments thereof by way of example and in which:

FIG. 1 shows a diagrammatic side view of an endoscope with a measuring device according to the invention, FIg. 2 shows a distal front view of the endoscope according to FIG. 1, FIG. 3 shows another identical front view with a supplementary measuring device, FIG. 4 shows the distal end of an endoscope with a spatial measuring device in side view with the individual measuring rays, and FIG. 5 shows a side view of the proximal end of the endoscope in the embodiment according to FIG. 3.

DETAILED DESCRIPTION OF PREFERRED EMBODIMENTS

Referring now to the drawings, according to the embodiment shown in FIGS. 1 and 2, with an endoscope with lateral objective a laser 1 is used for generating a thin and visible, preferably coloured light ray, e.g. an HeNe laser, the light ray of which is divided at a ratio of 50:50 by a splitting mirror 2 and fed to two laser fibres 3 and 4 which pass through two protective tubes 5 and 6 on the opposite sides of an endoscope shaft 7. However, it is also possible to let the laser fibres run through shaft 7 itself in guides. Instead of a single laser 1, two identical lasers 1 can also be used in which case splitter mirror 2 can be omitted. At the distal end the light rays are deflected in the region of the objective or objective lens 10 of the optical system of the endoscope on both sides, i.e. spaced apart from one another, by reflectors 8 and 9 in the form of a mirror or prism, as measuring rays.

The one measuring ray 11 deflected by the advantageously stationary reflector 9 is provided with a fixed and parallel or approximately parallel position with respect to the axis 12 of the objective lens which in the example is at an angle of 90° to the axis of the optical system.

The second reflector 8, on the other hand, is made rotatable by manipulating a proximal adjusting ring 13 with respect to a scale 13a, the measuring ray 14 emitted, however, remaining constantly in the plane of the measuring ray 11. This plane advantageously also passes through axis 12 of the objective lens. For measuring the distance of subject 15 from the objective or objective lens 10 the reflector 8 is adjusted so that the measuring ray 14 assumes a certain fixed angle with respect to axis 12 of the objective lens, e.g. runs parallel to the axis 12 of the objective lens. In this position of reflector 8, ring 13 is set to the zero position of scale 13a.

For distance measurement, reflector 8 is rotated by ring 13 until measuring ray 14 intersects measuring ray 11, forming an angle α at 16 in the plane of the subject which can be seen by means of the optical system by the visible and preferably coloured light of measuring rays 11, 14. The rotation of adjusting ring 13 then reproduces the angle of deflection of measuring ray 14, with respect to scale 13a, which is then converted into a length measurement with the aid of a table; or the scale can be calibrated right from the start in length measurements in dependence on the angle of measuring ray 14. In this way the distance of the subject from the objective lens can be read off scale 13a exactly. For illuminating the subject to be observed through the optical system with eyepiece 18 the proximally enlarged part 17 of the endoscope is provided in known manner with a connection 19 for the fibre optics of a projector.

It will be understood that the same measurement can also be performed with endoscopes with a straight or prograde objective lens and the endoscope can be equipped with a customary lens system or fibre-optical image transmission system.

Using the aforementioned optical distance measuring system, it is also possible to supplement the endoscope, as shown in FIG. 3 and 4, in such a way that length measurements can be performed on the subject, as well. For this purpose a further laser fibre runs next to light conductor 4, the light ray of which is deflected at the distal end next to reflector 8 in the plane of measuring rays 11 and 14 by a reflector 20 as measuring ray 21. According to FIG. 5, this reflector 20 can be rotated by a rotatable manipulator 22 with respect to scale 23. In this the length measurement a, for which first the distance measurement according to FIG. 1 and 2 is required, is based on a zero position of scale 23 with respect to a marking on the manipulator and a zero position of measuring ray 21. This zero position of measuring ray 21 is provided, for example, when measuring ray 21 is in the same plane as measuring ray 14, and particularly when measuring ray 14 is intersecting measuring ray 11 in the plane of the subject. By turning manipulator 22, reflector 20 is rotated and measuring ray 21 assumes an angular position $\beta$ with respect to measuring ray 14 as shown in FIG. 3. Angle $\beta$ can be read off scale 23 and can be read off a calibrating table as length a, or scale 23 is calibrated in units of length right from the start.

In the embodiments according to FIGS. 1 to 3, all measuring rays 11, 14 and 21 are in the same plane as axis 12 of the objective lens which simplifies conversion into units of length. According to the embodiment shown in FIG. 4, however, it is also possible to arrange reflectors 8, 9 and 20 next to objective lens 10 on one side only of the endoscope shaft or separated on two sides, but displaced in the longitudinal direction of shaft 7 in order to obtain the required spacing between fixed reflector 9 and reflectors 8 and 20.

For the embodiment according to FIGS. 4 and 5 the posibility exists to develop the deflection device in such a way, requiring more complicated mechanical arrangements, however, that measuring rays 11 and 21 can also be adjusted in planes vertical to the plane of measuring rays 11, 14, 21 with angle $\gamma$ so that the possibility exists then, also to measure subject lengths $a_1$ and $a_2$, and thus, finally, areas, apart from the distance of subject to objective and subject length a.

The measuring device can be arranged on an endoscope of the type hereinabove described in such a way that the two intersecting measuring rays 11, 14 assume a fixed angle with respect to one another. In this case it is necessary, however, to adjust the measuring device together with the optical system or the objective of the optical system in such a way that the point of intersection 16 of the measuring rays reaches the plane of the subject.

Finally, it is also possible to utilize the optical distance and/or length measuring device described in conjunction with any observation device desired, e.g. microscopes.

I claim:

1. An endoscope equipped with an optical system including an objective lens defining a field of view of said endoscope and incorporating a device for measuring the distance between a subject and the objective lens of the optical system of the endoscope and selected lengths along the surface of a subject, said device comprising means for providing first, second and third visible light rays adjacent said objective lens, said rays being such that when projected into the field of view of the endoscope and onto a subject within the viewing range of the endoscope each ray will form a spot of light on the surface of the subject visible through said objective lens and of a diameter which is a small fraction of the portion of the surface of the subject which is within the field of view, first, second, and a third discrete reflector means for deflecting said first, second and third light rays, respectively, into the field of view of said endoscope, said first and second reflector means being spaced from one another at the distal end of said endoscope next to said objective lens of said optical system, said first reflector means deflecting said first ray into a fixed and approximately parallel position with respect to the viewing axis of said objective lens, means for moving said second reflector means such that said second ray may be moved within a plane which includes said first ray from a position parallel to the viewing axis of said objective lens to a position wherein said second ray intersects said first ray at a point within the viewing range of said endoscope, a first scale operatively associated with said means for moving said second reflector means for indicating the angle of said second ray with respect to a position parallel to the viewing axis of said objective lens, means for moving said third reflector means such that said third ray may be moved within a plane which includes said first ray from a position wherein said third ray intersects said first ray at a point within the viewing range of said endoscope towards a position wherein said third ray is parallel to the viewing axis of said objective lens, a second scale operatively associated with said means for moving said third reflector means, said second scale being based on a zero angle position defined by the position of said third ray when the surface of a subject is being viewed within the viewing range of said endoscope and said first and third rays intersect one another in the plane of the surface, said second scale indicating the distance along the surface of a subject being viewed between the spot on the surface caused by said first ray and the spot on the surface caused by said third ray.

* * * * *